US012806032B2

(12) United States Patent
Berry

(10) Patent No.: US 12,806,032 B2
(45) **Date of Patent: *Nov. 24, 2026**

(54) EXPANDABLE IMPLANT

(71) Applicant: Bret Michael Berry, Tallahassee, FL (US)

(72) Inventor: Bret Michael Berry, Tallahassee, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/974,764

(22) Filed: Dec. 9, 2024

(65) Prior Publication Data

US 2025/0099258 A1 Mar. 27, 2025

Related U.S. Application Data

(63) Continuation of application No. 17/959,283, filed on Oct. 3, 2022, now Pat. No. 12,161,559, which is a continuation of application No. 17/164,982, filed on Feb. 2, 2021, now Pat. No. 11,458,024.

(51) Int. Cl.
*A61F 2/44* (2006.01)
*A61F 2/30* (2006.01)

(52) U.S. Cl.
CPC .. *A61F 2/4425* (2013.01); *A61F 2002/30523* (2013.01)

(58) Field of Classification Search
CPC ........ A61F 2/4455; A61F 2/445; A61F 2/446; A61F 2/4465; A61F 2/447; A61F 2002/30523; A61F 2002/3037; A61F 2002/30383; A61F 2002/30522; A61F 2002/30593; A61F 2002/3052
USPC ........................................... 623/17.11–17.16
See application file for complete search history.

(56) References Cited

U.S. PATENT DOCUMENTS

| | | | | |
|---|---|---|---|---|
| 10,159,583 | B2 * | 12/2018 | Dietzel | A61F 2/4657 |
| 2014/0277470 | A1 * | 9/2014 | Baynham | A61F 2/447 623/17.13 |
| 2016/0199192 | A1 * | 7/2016 | McLaughlin | A61F 2/446 623/17.16 |
| 2017/0319350 | A1 * | 11/2017 | Mclaughlin | A61F 2/446 |

FOREIGN PATENT DOCUMENTS

| | | | | |
|---|---|---|---|---|
| WO | WO-2008112923 A1 * | 9/2008 | | A61F 2/44 |

* cited by examiner

*Primary Examiner* — Eduardo C Robert
*Assistant Examiner* — Tara Rose E Carter
(74) *Attorney, Agent, or Firm* — Sigma Law Group LLC

(57) ABSTRACT

An implant is disclosed. The implant has a base including an extension arm cavity and a ratchet block cavity that intersects the extension arm cavity, an extension arm that is movably disposed in the extension arm cavity, and a ratchet block that is movably disposed between a first position and a second position in the ratchet block cavity. The ratchet block when disposed in the first position allows movement of the extension arm in an upward direction out of the extension arm cavity and blocks movement of the extension arm in a downward direction into the extension arm cavity. The ratchet block when disposed in the second position allows movement of the extension arm both in the upward direction out of the extension arm cavity and the downward direction into the extension arm cavity.

20 Claims, 9 Drawing Sheets

EXPANDABLE IMPLANT

CROSS-REFERENCE TO RELATED APPLICATIONS

This application is a continuation of U.S. application Ser. No. 17/959,283, entitled “Expandable Implant”, filed on Oct. 3, 2022, now U.S. Pat. No. 12,161,559, issued on Dec. 10, 2024, which is a continuation of U.S. application Ser. No. 17/164,982, entitled “Expandable Implant”, filed on Feb. 2, 2021, now U.S. Pat. No. 11,458,024, issued on Oct. 4, 2022, the entire disclosure of each of which is incorporated herein by reference.

TECHNICAL FIELD

The present disclosure is directed to an implant, and more particularly, to an expandable implant.

BACKGROUND OF THE DISCLOSURE

Conventional corpectomy devices are used to treat conditions, injuries, and diseases that degrade a functioning of the spinal column. Corpectomy devices are typically used to decompress spinal nerves and the spinal cord.

Conventional corpectomy devices include expandable corpectomy devices. Such expandable corpectomy devices may use a rack and gear assembly or a turnbuckle or threaded mechanism for expansion. Conventional corpectomy devices that use a rack and gear assembly typically have a single rack and gear, which can lead to the device skewing to one side during expansion. Conventional corpectomy devices that use rack and gear expandable devices may utilize a ratchet or other mechanism to prevent unwanted collapse. However, such conventional corpectomy devices are unable to turn the ratchet off if the device is over-expanded or is to be collapsed for removal or replacement.

The exemplary disclosed system and method of the present disclosure is directed to overcoming one or more of the shortcomings set forth above and/or other deficiencies in existing technology.

SUMMARY OF THE DISCLOSURE

In one exemplary aspect, the present disclosure is directed to an implant. The implant includes a base including an extension arm cavity and a ratchet block cavity that intersects the extension arm cavity, an extension arm that is movably disposed in the extension arm cavity, and a ratchet block that is movably disposed between a first position and a second position in the ratchet block cavity. The ratchet block when disposed in the first position allows movement of the extension arm in an upward direction out of the extension arm cavity and blocks movement of the extension arm in a downward direction into the extension arm cavity. The ratchet block when disposed in the second position allows movement of the extension arm both in the upward direction out of the extension arm cavity and the downward direction into the extension arm cavity.

In another aspect, the present disclosure is directed to a method. The method includes providing a base including an extension arm cavity and a ratchet block cavity that intersects the extension arm cavity, movably disposing an extension arm in the extension arm cavity, movably disposing a ratchet block between a first position and a second position in the ratchet block cavity, allowing movement of the extension arm in an upward direction out of the extension arm cavity and blocking movement of the extension arm in a downward direction into the extension arm cavity by disposing the ratchet block in the first position, and allowing movement of the extension arm both in the upward direction out of the extension arm cavity and the downward direction into the extension arm cavity by disposing the ratchet block in the second position.

BRIEF DESCRIPTION OF THE DRAWINGS

Accompanying this written specification is a collection of drawings of exemplary embodiments of the present disclosure. One of ordinary skill in the art would appreciate that these are merely exemplary embodiments, and additional and alternative embodiments may exist and still within the spirit of the disclosure as described herein.

DETAILED DESCRIPTION AND INDUSTRIAL APPLICABILITY

Figure 1:
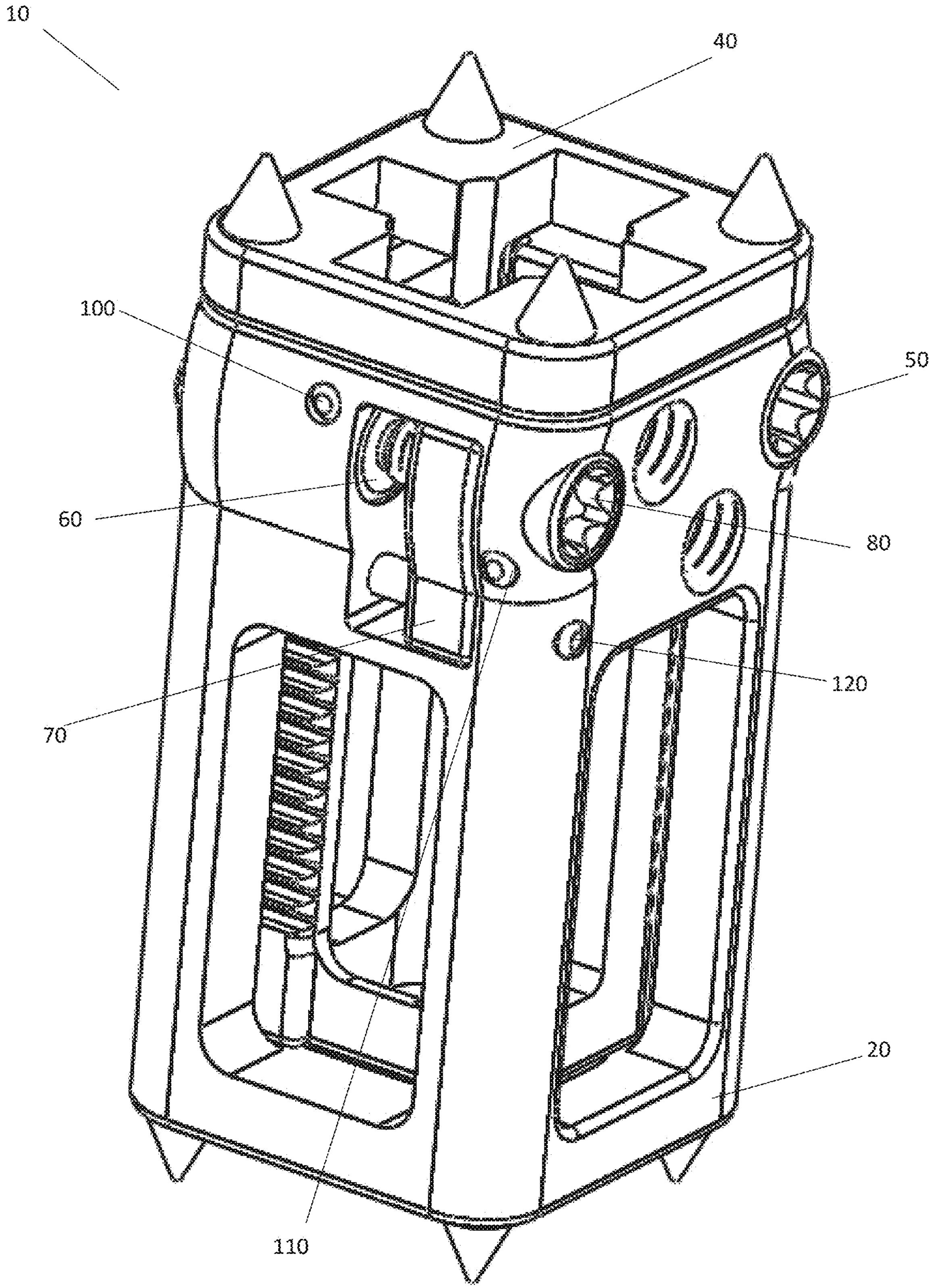
FIG. 1 illustrates a perspective view of an exemplary device in collapsed position, with ratchet in a first position (e.g., prevention position)
Figure 2:
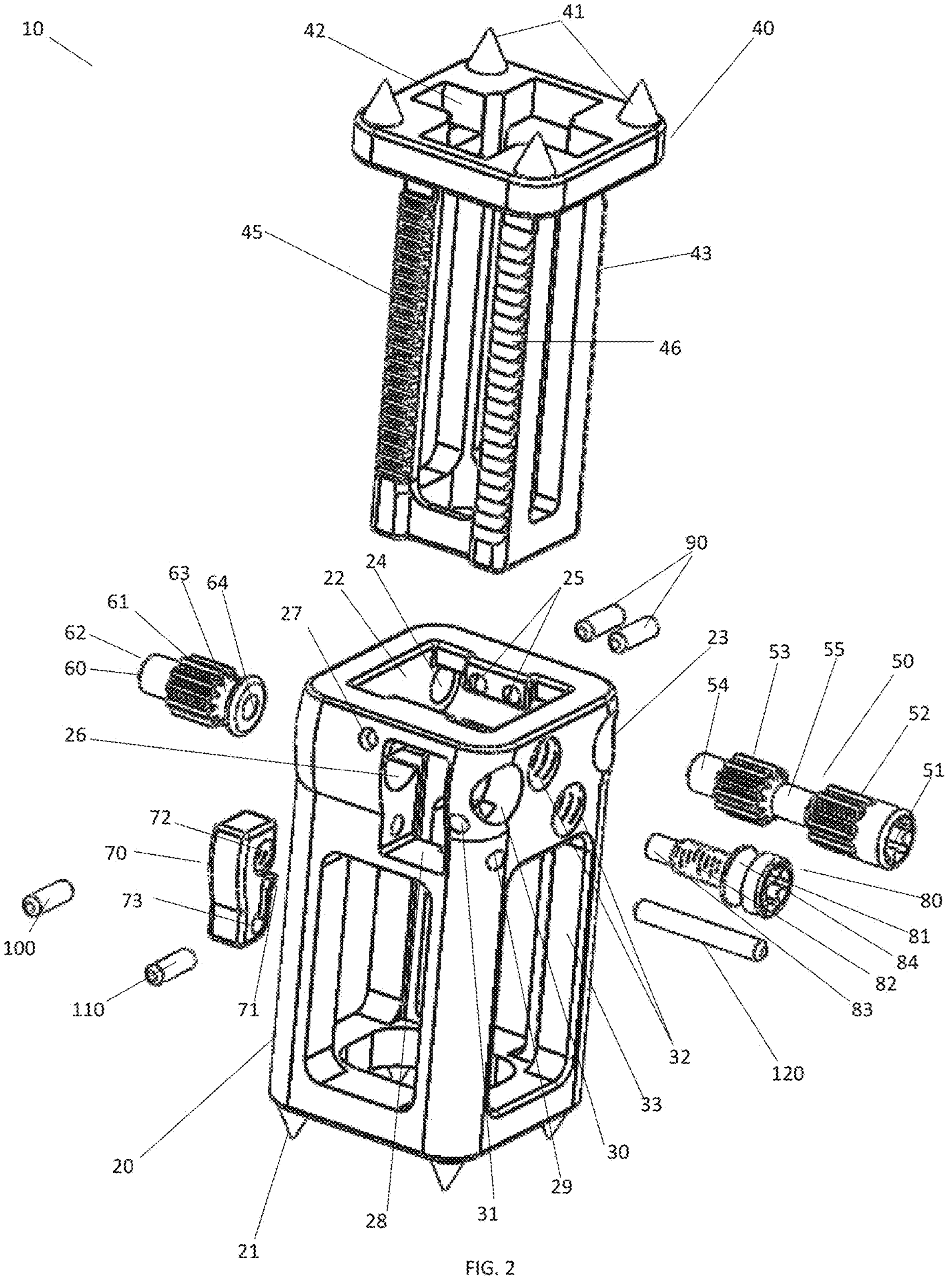
FIG. 2 illustrates an exploded view of the exemplary disclosed device.

The exemplary disclosed system, apparatus, and method may include an expandable implant. For example, the exemplary disclosed system, apparatus, and method may be an expandable corpectomy device. In at least some exemplary embodiments, the exemplary disclosed system, apparatus, and method may be an expandable corpectomy device with selectable ratchet.

In at least some exemplary embodiments, the exemplary disclosed system, apparatus, and method may be a corpectomy implant that may expand upward utilizing a rack and gear assembly or mechanism. The exemplary disclosed implant may have a ratchet mechanism that may substantially prevent undesirable (e.g., unwanted) collapse of the device after the device has been expanded. The exemplary disclosed ratchet mechanism may be movable to allow for the device to be collapsed if desired, to be repositioned, to alter a final height of the device, and/or to allow for removal of the device. The exemplary disclosed implant may be formed from any suitable material for providing an implant such as, for example, titanium, cobalt chrome, nitinol, stainless steel, tantalum, bioceramic material (e.g., alumina and zirconia), polyetheretherketone, and/or any other suitable materials for providing an implant.

FIGS. 1-13 illustrate an exemplary embodiment of the exemplary disclosed system, apparatus, and method. An expandable implant 10 may include two main components, a base 20, and an extension arm 40. The base 20 may have an internal extension arm cavity 22 within which the extension arm 40 is disposed (e.g., sits). Extension arm 40 may translate upward or superiorly within the extension arm cavity 22. The extension arm cavity 22 of the base 20 may prevent the extension arm 40 from rotating.

The base 20 may be a rectangular cube (e.g., or any other suitable shape) with protrusions such as spikes 21 or any other suitable anti-migration features. Spikes 21 may be disposed on the lower, or inferior, face of base 20. Spikes 21 may contact or abut (e.g., dig into) a vertebral endplate. The upper, or superior, face of the base 20 may include (e.g., be defined by) an extension arm cavity 22 which may be substantially (e.g., roughly) the same shape and size as the extension arm 40, allowing the extension arm 40 to slide down into the base 20. The anterior, or proximal, face of the base 20 may include two apertures (e.g., large holes) on the upper, lateral portions. The first hole, on what may be the implant's 10 (e.g., and patient's) left may be a main gear front aperture 23. Main gear front aperture 23 may be a cylindrical hole that extends (e.g., runs) from the anterior face of the base 20 to the back of the extension arm cavity 22. Additionally, the main gear front aperture 23 may also intersect the extension arm cavity 22. A main gear rear aperture 24 may extend along the same axis as the main gear front aperture 23 from the back face of the extension arm cavity 22 to the posterior face of the base 20. The main gear rear aperture 24 may be slightly smaller in diameter than main gear front aperture 23. A main gear 50 may fit inside these two main gear apertures 23, 24, allowing the main gear 50 to rotate axially within them. A rear nub 54 of the main gear 50 may fit inside the main gear rear aperture 24 to allow two points of contact for the elongated cylindrical main gear 50, as well as preventing the main gear 50 from being forced posteriorly. A pair of main gear retaining pin holes 25 may be disposed on the left lateral face of the base 20. The pair of main gear retaining pin holes 25 may intersect the main gear front aperture 23. A pair of main gear retaining pins 90 may be inserted into these main gear retaining pin holes 25 and in turn may seat into a retaining pin recess 55 of the main gear 50, which may prevent main gear 50 from being removed from the base 20.

The main gear 50 may include (e.g., may be defined by) a drive feature 51 disposed on the anterior face, which may allow a user (e.g., a surgeon) to turn the main gear 50. The main gear 50 may also include (e.g., may be defined by) a set of front gear teeth 52 and rear gear teeth 53, separated by the retaining pin recess 55. The rear nub 54 may be disposed at the posterior end of the main gear 50. The front gear teeth 52 of the main gear 50 may mesh with a front main rack 43 of the extension arm 40. Likewise, the rear gear teeth 53 of the main gear 50 may mesh with a rear main rack 44 of the extension arm 40. As the main gear 50 rotates, it may thereby move the extension arm 40 up and down in relation to the base 20.

A ratchet drive aperture 30 may be disposed on the right, upper, lateral portion of the front face of the base 20. The ratchet drive aperture 30 may extend to and align with a secondary gear aperture 26. A secondary gear 60 may be inserted through the ratchet drive aperture 30 and inserted into the secondary gear aperture 26, where the secondary gear 60 may be able to rotate. Both the ratchet drive aperture 30 and the secondary gear aperture 26 may intersect the extension arm cavity 22. The rear of the secondary gear aperture 26 may narrow to hold a rear nub 62 of the secondary gear 60 and to prevent the secondary gear 60 from being pushed unsuitably (e.g., too far) posteriorly. A secondary gear retaining pin hole 27 may be disposed on the right lateral face of the base 20. The secondary gear retaining pin hole 27 may intersect the secondary gear aperture 26. A secondary gear retaining pin 100 may be inserted into the secondary gear retaining pin hole 27 and in turn may seat into a retaining pin groove 63 of the secondary gear 60, which may prevent the secondary gear 60 from being removed from the base 20.

The secondary gear 60 may include (e.g., may be defined by) a ratchet drive aperture 64 disposed on the anterior face, which may allow a rear nub 83 of a ratchet drive 80 to seat into the secondary gear 60. The secondary gear 60 may also include (e.g., may be defined by) a set of gear teeth 61, which may be posterior (e.g., just posterior) of the retaining pin groove 63. A rear nub 62 may be disposed at the posterior end of the secondary gear 60. The gear teeth 61 of the secondary gear 60 may mesh with a secondary rack 45 of the extension arm 40. As the extension arm 40 translates within the base 20, the extension arm 40 may turn the secondary gear 60, thereby providing (e.g., ensuring) that the extension arm 40 moves straight.

Figure 3:
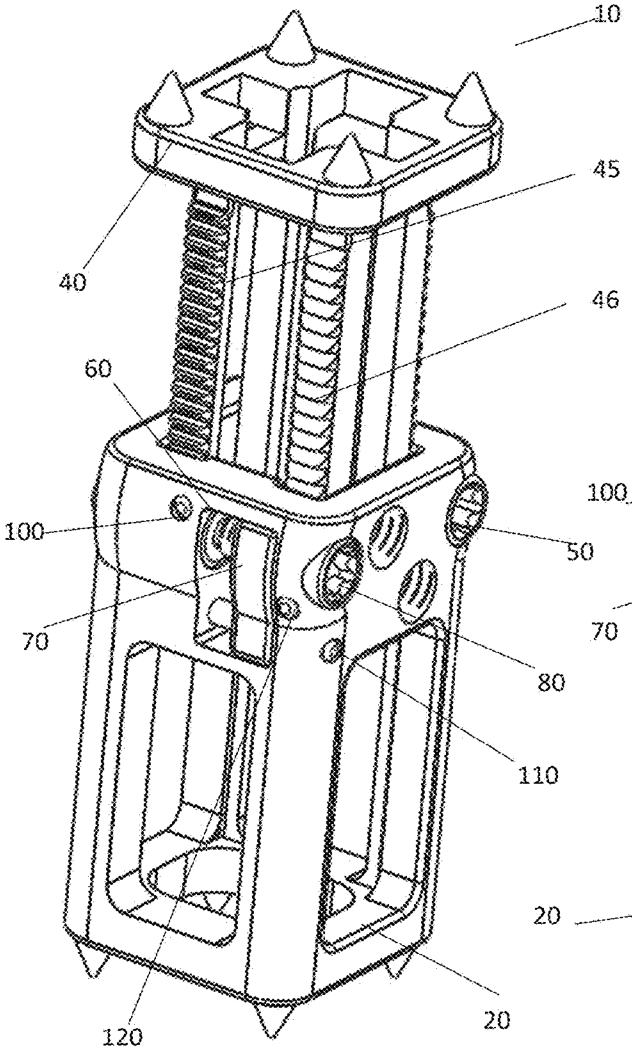
FIG. 3 illustrates a perspective view of the exemplary disclosed device in expanded position, with ratchet in the first position (e.g., prevention position)
Figure 4:
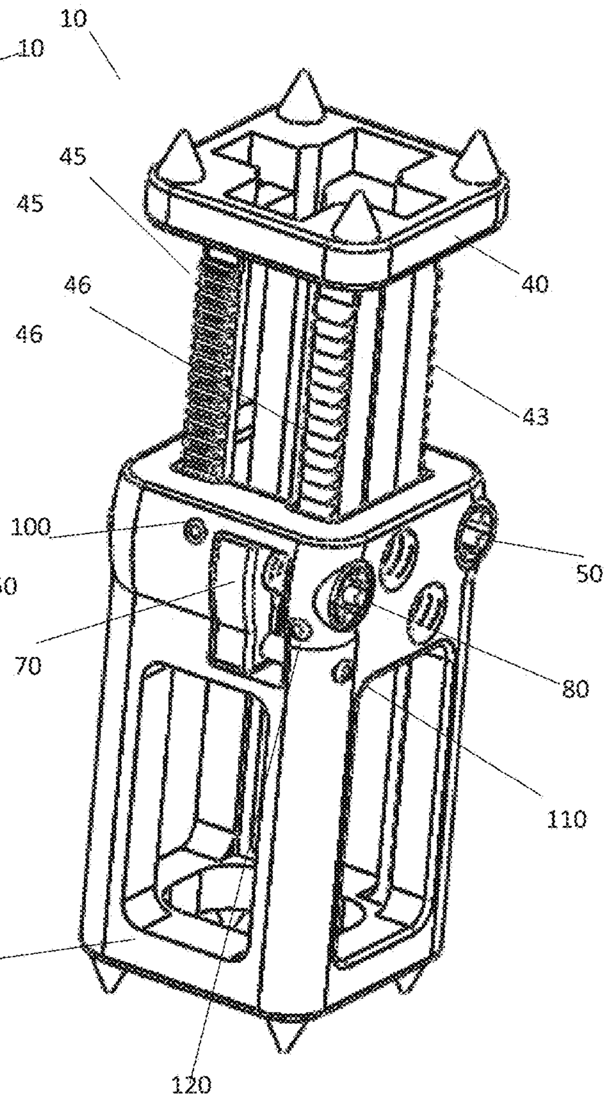
FIG. 4 illustrates a perspective view of the exemplary disclosed device in expanded position, with ratchet in a second position (e.g., non-prevention position)
Figure 5:
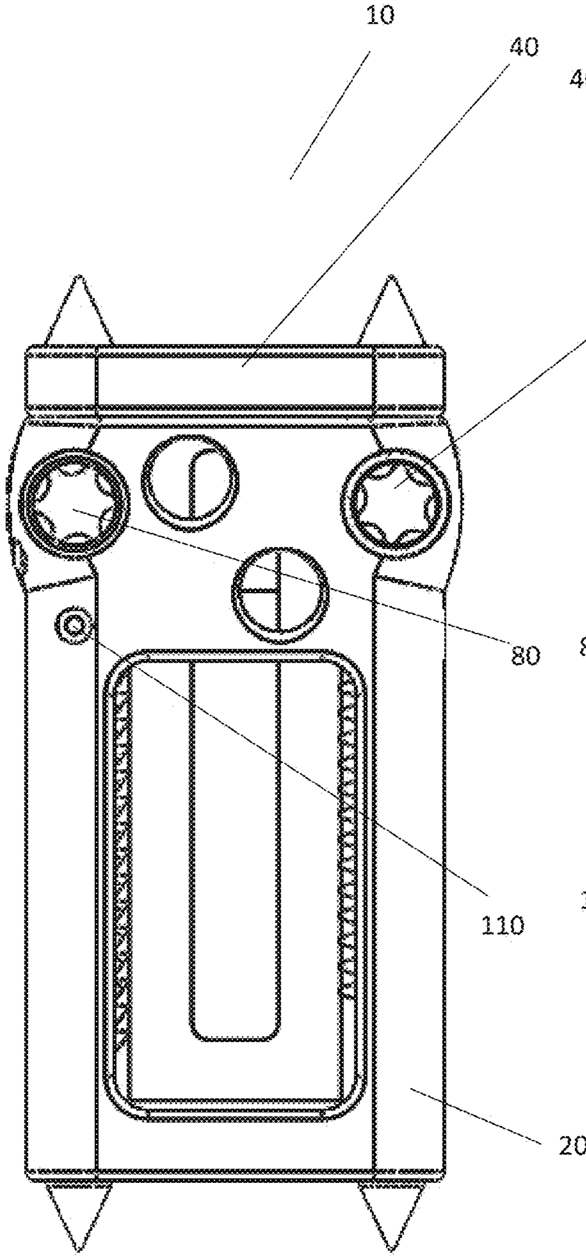
FIG. 5 illustrates an anterior view of the exemplary disclosed device in collapsed position.
Figure 6:
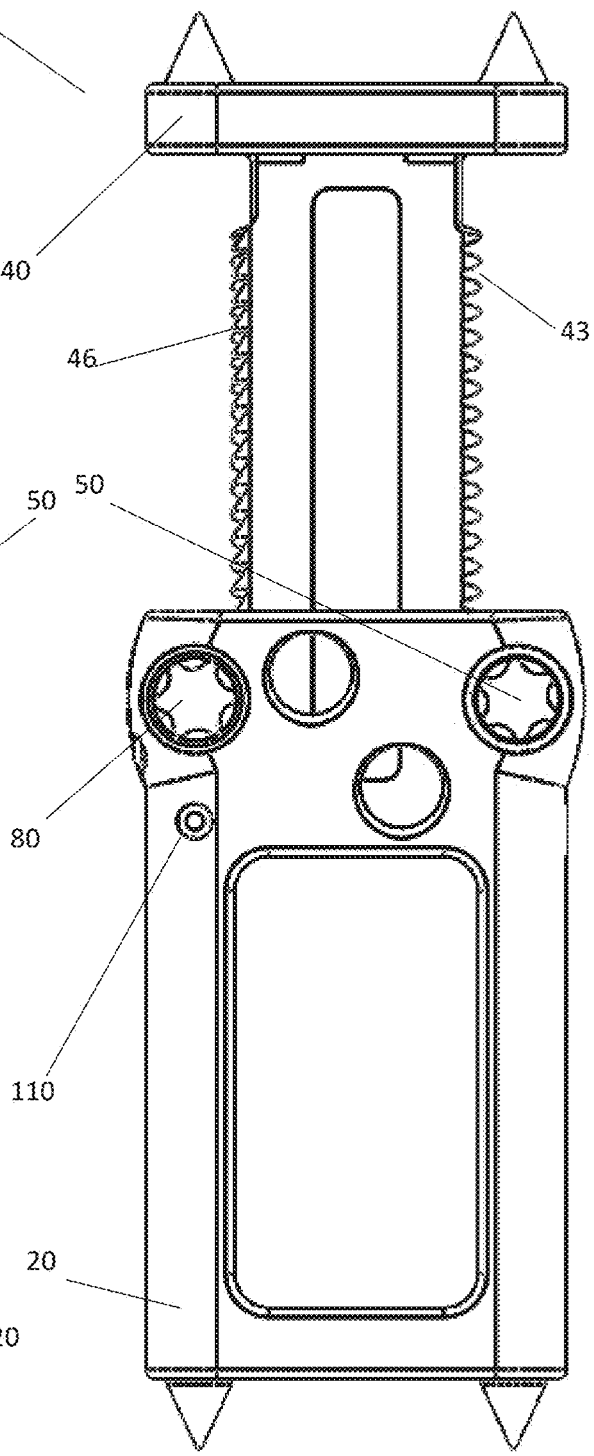
FIG. 6 illustrates an anterior view of the exemplary disclosed device in expanded position.
Figure 7:
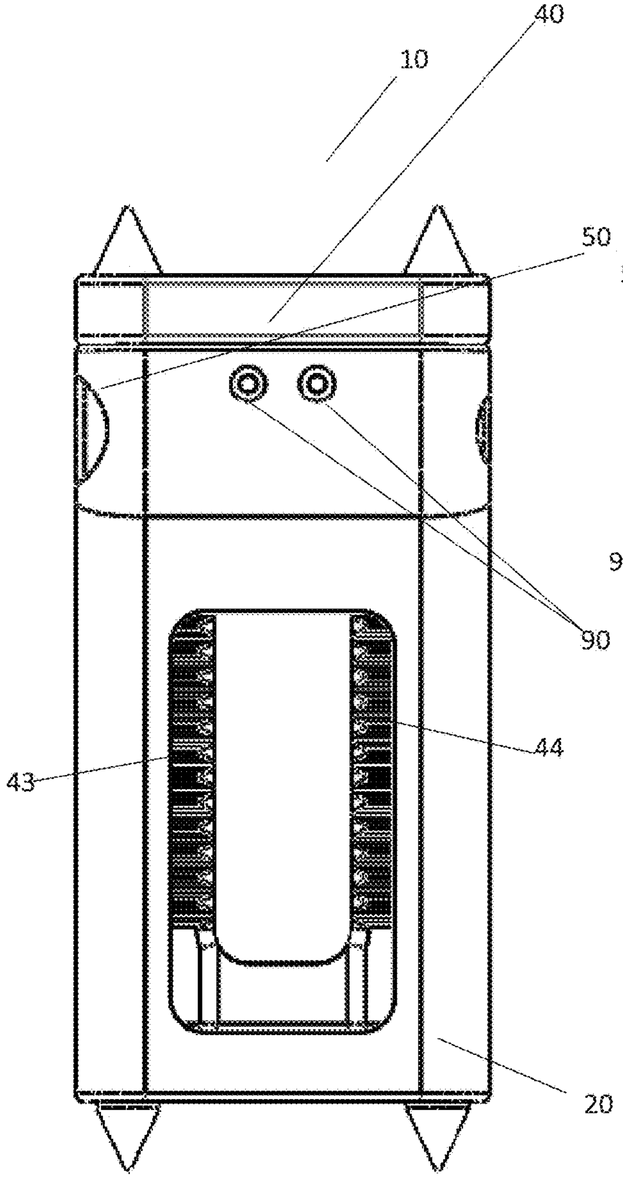
FIG. 7 illustrates a left lateral view of the exemplary disclosed device in collapsed position.
Figure 8:
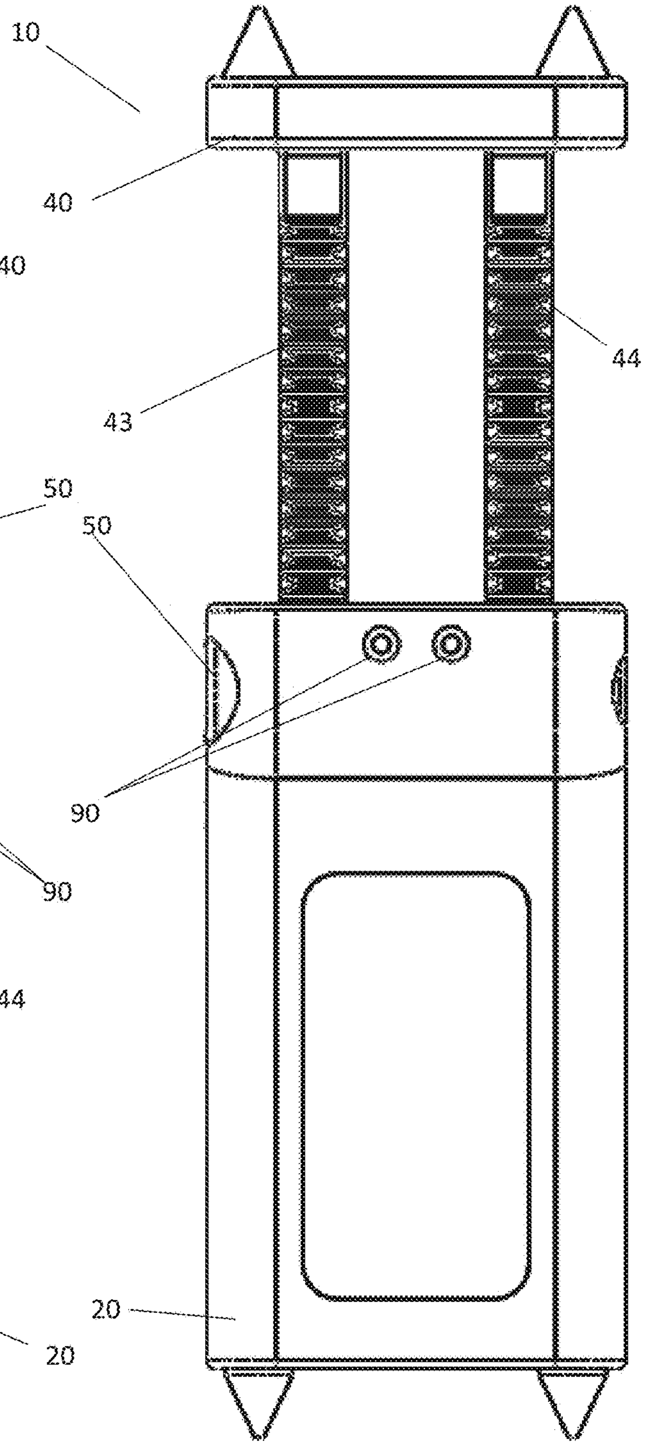
FIG. 8 illustrates a left lateral view of the exemplary disclosed device in expanded position.
Figure 9:
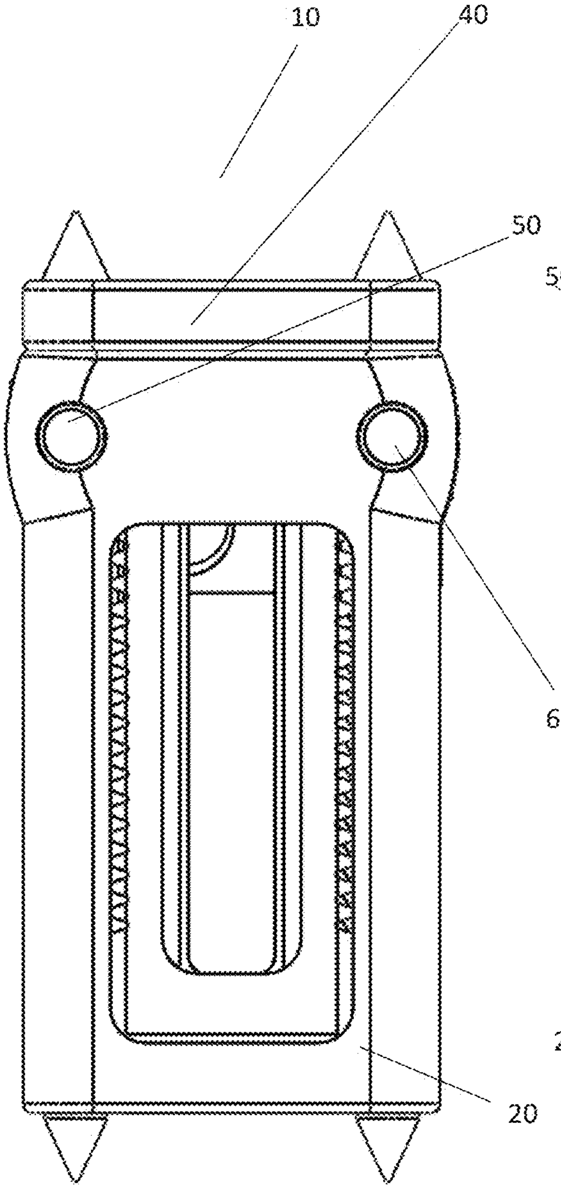
FIG. 9 illustrates a posterior view of the exemplary disclosed device in collapsed position.
Figure 10:
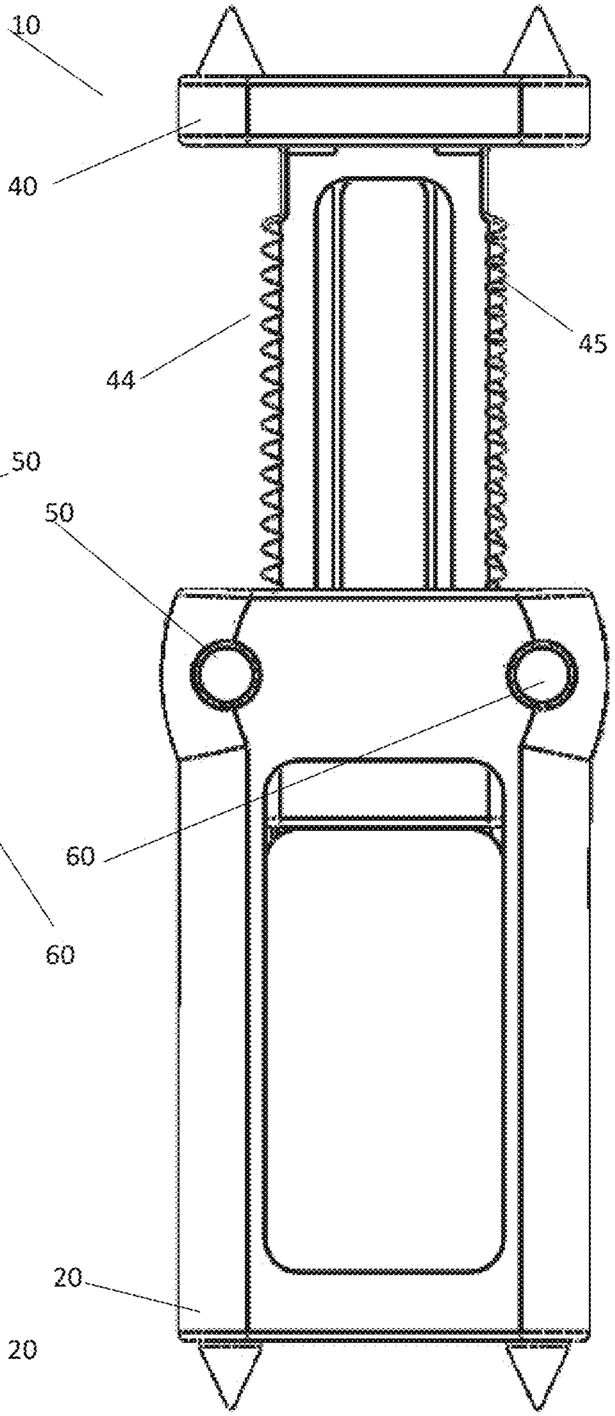
FIG. 10 illustrates a posterior view of the exemplary disclosed device in expanded position.
Figure 11:
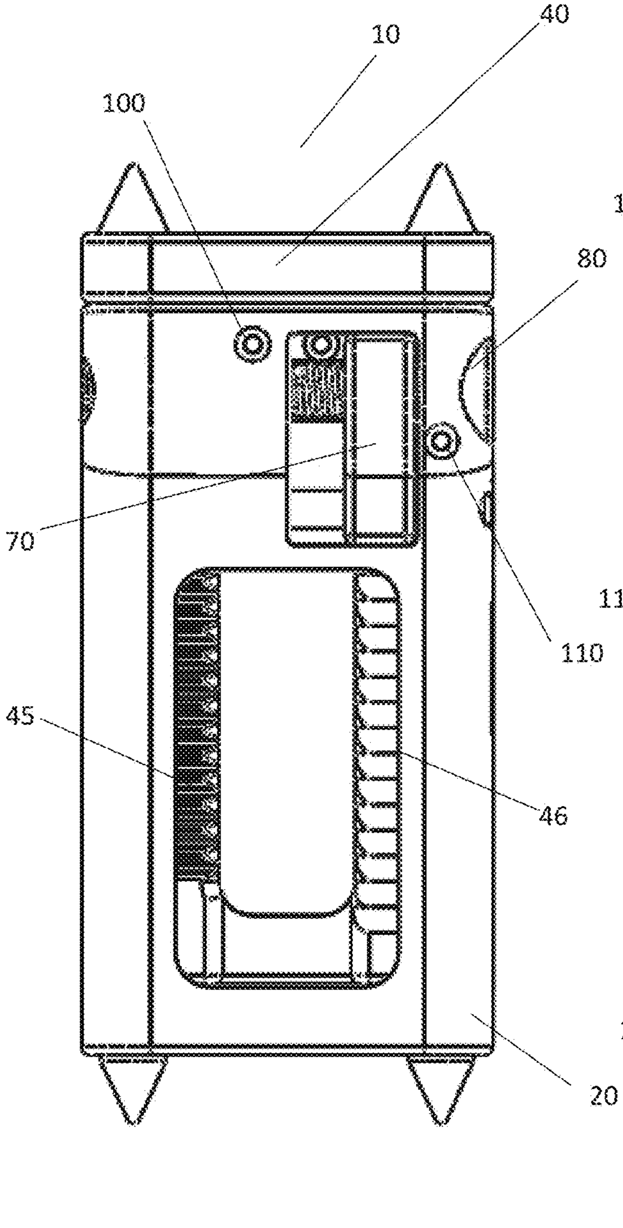
FIG. 11 illustrates a right lateral view of the exemplary disclosed device in collapsed position, with ratchet in prevention position.
Figure 12:
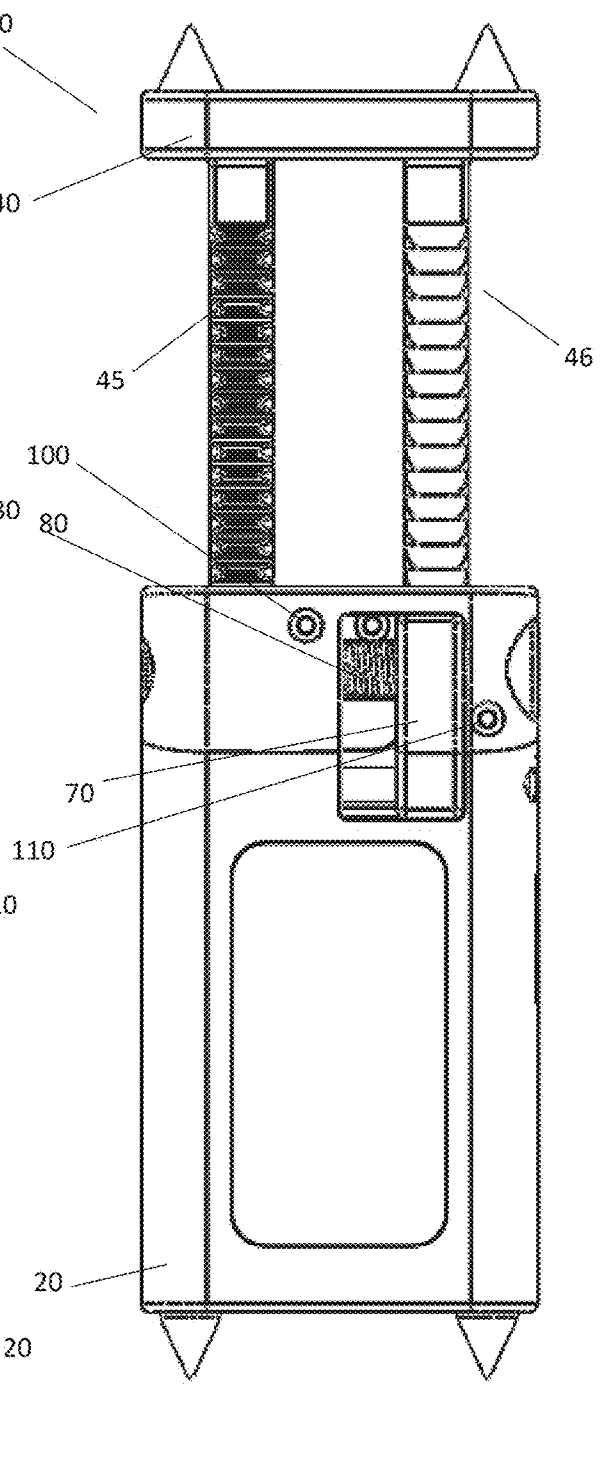
FIG. 12 illustrates a right lateral view of the exemplary disclosed device in expanded position, with ratchet in prevention position.
Figure 13:
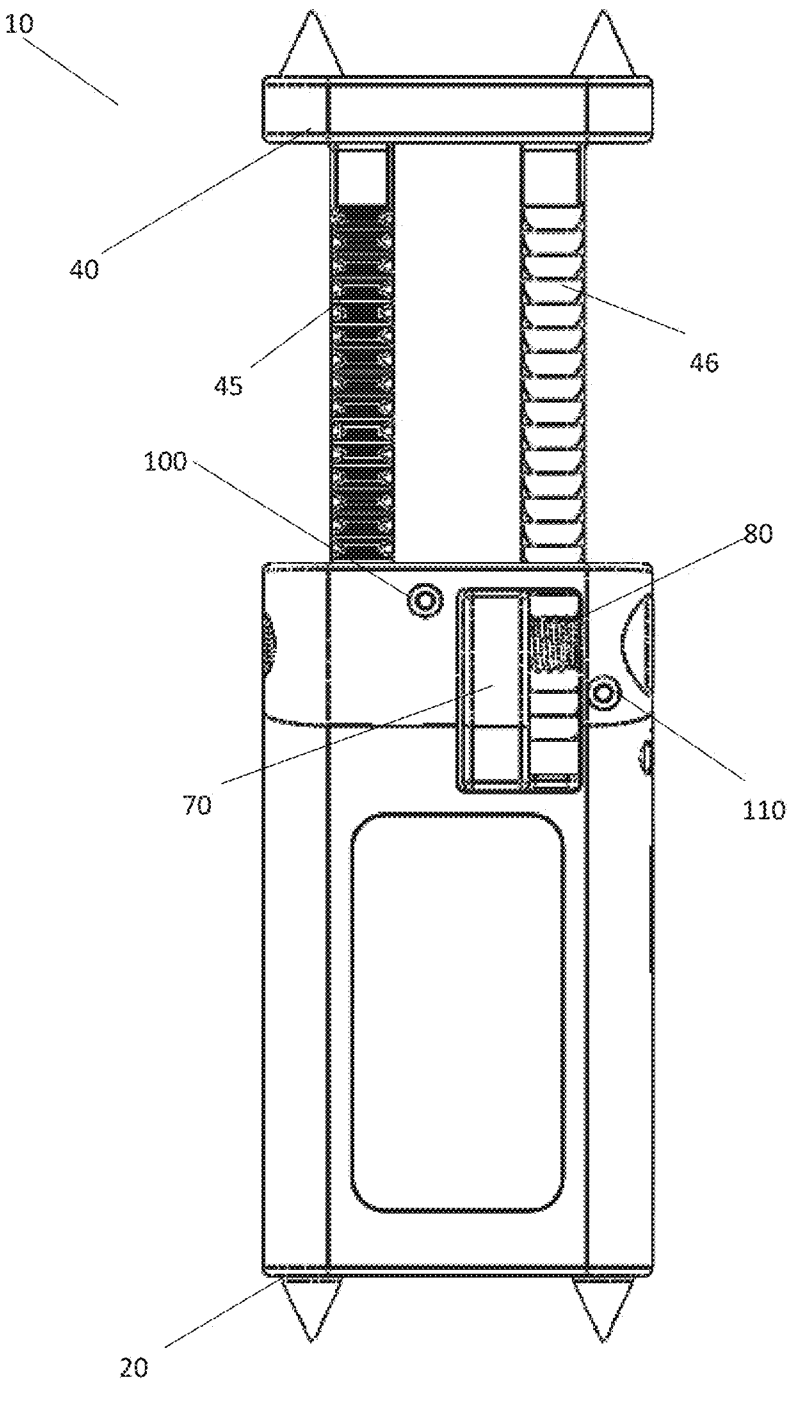
FIG. 13 illustrates a right lateral view of the exemplary disclosed device in expanded position, with ratchet in non-prevention position.

A rectangular ratchet block cavity 28 may be disposed on the right lateral face of the base 20. The rectangular ratchet block cavity 28 may intersect both the ratchet drive aperture 30 as well as the extension arm cavity 22. Additionally, a ratchet block retaining pin hole 29, which may extend posteriorly from the anterior face of the base 20, parallel to the ratchet drive aperture 30, may intersect the ratchet block cavity 28. A ratchet block 70 may be disposed (e.g., may sit) within the ratchet block cavity 28. The ratchet block 70 may be able to translate anteriorly-posteriorly within the ratchet block cavity 28. The ratchet block 70 may be held in place by the ratchet drive 80 and a ratchet block retaining pin 120. The upper portion of the ratchet block 70 may have an aperture including fasteners (e.g., threads 72), through which fasteners (e.g., threads 82) of the ratchet drive 80 may be received (e.g., may go through). A lower portion of the ratchet block 70 may include (e.g., may be defined by) a ratchet arm 71 and a retaining pin hole 73. The ratchet block retaining pin 120 may be received by (e.g., may go through) the retaining pin hole 73 of the ratchet block 70, and may prevent the ratchet block 70 from spinning or rotating as the ratchet drive 80 is turned. For example, as the ratchet drive 80 is turned, the ratchet drive 80 may cause (e.g., may force) the ratchet block 70 to translate within the ratchet block cavity 28. The ratchet arm 71 of the ratchet block 70 may be a flexible member that is flat on its top, and angled from underneath. The ratchet arm 71 may be formed from any suitable flexible material and/or may be configured to act flexibly (e.g., as a cantilever and/or any other suitable flexible configuration). For example, ratchet arm 71 may be formed from similar material as the exemplary disclosed materials described herein and may be configured to act flexibly (e.g., configured with a cantilever portion). The ratchet arm 71 may interact with a ratchet rack 46 of the extension arm 40 while the ratchet block 70 is in its anterior most position (e.g., as illustrated in the first position or prevention position of the ratchet block 70 in FIG. 3). When the ratchet block 70 is moved to its posterior most position within the ratchet block cavity 28, the ratchet block 70 may no longer contact (e.g., touch) the ratchet rack 46 of the extension arm 40 (e.g., as illustrated in the second position or non-prevention position of the ratchet block 70 in FIG. 4). Because the teeth of the ratchet rack 46 may be flat on the bottom and angled on the top, the ratchet arm 71 may prevent the extension arm 40 from retracting into the base 20 after it has been expanded, while the ratchet block 70 is in the anterior position. The flat surface of the ratchet arm 71 may abut (e.g., bear) against the flat surface of one of the teeth of the ratchet rack 46 to prevent the extension arm 40 from moving downward into the extension arm cavity 22. The flexible ratchet arm 71 may flexibly move based on contact between the angled surface of the ratchet arm 71 and the angled surface of one of the teeth of the ratchet rack 46. For example, an end portion of ratchet arm 71 may engage with (e.g., catch) a tooth of ratchet rack 46. The extension arm 40 may move upwards (e.g., only move upwards) within the base 20 while the ratchet block 70 is in this anterior or first position. However, when the ratchet block 70 is moved to the posterior or second position, the extension arm 40 may be moved both up and down within the base 20. The ratchet block 70 may move in a first direction between the first and second position (e.g., as illustrated in FIGS. 3 and 4) that may be perpendicular to the upward and downward direction of the movement of the extension arm 40.

The ratchet drive 80 may extend through the ratchet block 70. A drive feature 81 may be disposed on the anterior face of the ratchet drive 80, which may allow a user (e.g., a surgeon) to turn the ratchet drive 80. A retaining pin groove 84 may be disposed posterior of (e.g., just posterior of) the drive feature 81. A ratchet drive retaining pin 110, which may be inserted through a ratchet drive retaining pin hole 31 disposed at (e.g., on) the lateral face of the base 20, may be disposed within (e.g., may be seated within) the retaining pin groove 84, thereby substantially preventing (e.g., preventing) the ratchet drive 80 from translating within the base 20. The threads 82 may be disposed posterior of the retaining pin groove 84, which may drive the ratchet block 70 forward and backward. The posterior portion of the ratchet drive 80 may include the rear nub 83, which may be received in (e.g., may seat into) the ratchet drive aperture 64 of the secondary gear 60. The rear nub 83 may provide rotation contact (e.g., two points of rotation contact) for the ratchet drive 80, while still allowing the ratchet drive 80 and secondary gear 60 to rotate independently of one another.

The lower anterior face of the base 20 may include (e.g., may be defined by) an anterior aperture 33. As the extension arm 40 is extended upward, the extension arm 40 may vacate the lower portion of the extension arm cavity 22, creating a void. The anterior aperture 33 may allow a user (e.g., a surgeon) to pack bone graft into this void after the extension arm 40 has been extended, thereby aiding in the fusion during a procedure. The posterior and lateral faces of the base 20 may be solid, or may have windows (e.g., large windows as shown), small holes, or a porous structure 34*a*, for example as shown in an implant 10*a* (e.g., including a base 20*a* with porous structure that may be similar to base 20, and an extension arm 40*a* with porous structure that may be similar to extension arm 40) of FIG. 14.

Figure 14:
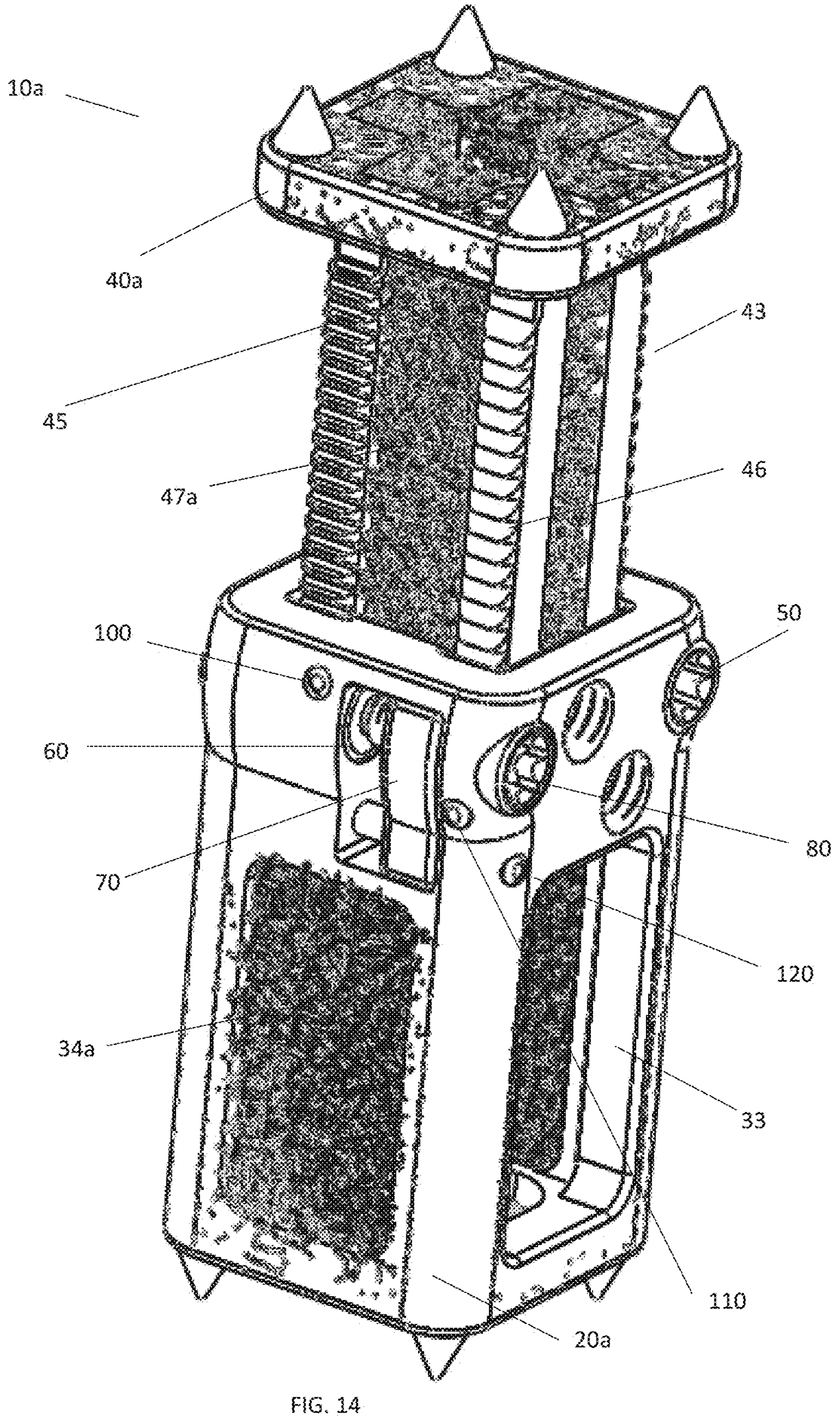
FIG. 14 illustrates a perspective view of another exemplary disclosed device in expanded position, with ratchet in prevention position.

The extension arm 40 may be an elongated rectangular cube having spikes 41 (e.g., and/or other anti-migration features) disposed on the upper, or superior, face. The spikes 41 may dig into a vertebral endplate. A graft aperture 42 may also extending from the upper face, into the extension arm 40. Bone graft may be packed into the graft aperture 42. The left side of the extension arm 40 may include (e.g., may be defined by) the front main rack 43 and the rear main rack 44. The right side of the extension arm 40 may include (e.g., may be defined by) the secondary rack 45 on the posterior corner and the ratchet rack 46 on the front corner. The anterior, posterior, and lateral faces of the extension arm 40 may be solid, or have windows (e.g., large windows as shown), small holes, or a porous structure 47*a*, for example as shown in FIG. 14.

The exemplary disclosed system, apparatus, and method may be used in any suitable application involving a spinal surgical procedure. For example, the exemplary disclosed system, apparatus, and method may be used in any suitable application involving a corpectomy or a vertebrectomy. The exemplary disclosed system, apparatus, and method may be used in any suitable application involving providing an implant device. The exemplary disclosed system, apparatus, and method may be used in any suitable application involving providing a corpectomy device.

A list of exemplary parts of the exemplary disclosed system, apparatus, and method is provided below:

10—implant
10*a*—second preferred implant
20—base
20*a*—base with porous structure
21—spikes
22—extension arm cavity
23—main gear front aperture
24—main gear rear aperture
25—main gear retaining pin holes
26—secondary gear aperture
27—secondary gear retaining pin hole
28—ratchet block cavity
29—ratchet block retaining pin hole
30—ratchet drive aperture
31—ratchet drive retaining pin hole
32—inserter/set screw holes
33—anterior aperture
34*a*—porous structure
40—extension arm
40*a*—extension arm with porous structure
41—spikes
42—graft aperture
43—front main rack
44—rear main rack
45—secondary rack
46—ratchet rack
47*a*—porous structure
50—main gear
51—drive feature
52—front gear teeth
53—rear gear teeth
54—rear nub
55—retaining pin recess
60—secondary gear
61—gear teeth
62—rear nub
63—retaining pin groove
64—ratchet drive aperture
70—ratchet block
71—ratchet arm

72—threads
73—retaining pin hole
80—ratchet drive
81—drive feature
82—threads
83—rear nub
84—retaining pin groove
90—main gear retaining pin
100—secondary gear retaining pin
110—ratchet drive retaining pin
120—ratchet block retaining pin In at least some exemplary embodiments, the exemplary disclosed implant may include a base (e.g., base 20 or base 20*a*) including an extension arm cavity and a ratchet block cavity that intersects the extension arm cavity, an extension arm (e.g., extension arm 40 or extension arm 40*a*) that is movably disposed in the extension arm cavity, and a ratchet block (e.g., ratchet block 70) that is movably disposed between a first position and a second position in the ratchet block cavity. The ratchet block when disposed in the first position may allow movement of the extension arm in an upward direction out of the extension arm cavity and may block movement of the extension arm in a downward direction into the extension arm cavity. The ratchet block when disposed in the second position may allow movement of the extension arm both in the upward direction out of the extension arm cavity and the downward direction into the extension arm cavity. The ratchet block may include a flexible ratchet arm and the extension arm may include a ratchet rack. The flexible ratchet arm may be aligned with the ratchet rack when the ratchet block is disposed in the first position. The ratchet rack may include a plurality of teeth, each of the plurality of teeth including a flat surface facing downward into the extension arm cavity and an angled surface facing upward away from the extension arm cavity. The flexible ratchet arm may include a flat surface facing upward away from the extension arm cavity and an angled surface facing downward into the extension arm cavity. The exemplary disclosed implant may also include a ratchet drive that is rotatably received in a ratchet drive aperture of the base and an aperture of the ratchet block. The ratchet drive may include ratchet drive threads that are threadable with ratchet block threads of the aperture of the ratchet block. The ratchet block may translate between the first position and the second position in the ratchet block cavity based on a rotation of the ratchet drive. The exemplary disclosed implant may further include a secondary gear that is rotatably received in a secondary gear aperture of the base that is aligned with the ratchet drive aperture, the secondary gear including a ratchet drive aperture configured to receive a rear nub of the ratchet drive. The secondary gear may include gear teeth that are configured to mesh with a secondary rack of the extension arm. The ratchet drive may rotate independently of the secondary gear. The ratchet block may move in a first direction between the first and second position that is perpendicular to the upward and downward direction of the movement of the extension arm.

In at least some exemplary embodiments, the exemplary disclosed method may include providing a base (e.g., base 20 or base 20*a*) including an extension arm cavity and a ratchet block cavity that intersects the extension arm cavity, movably disposing an extension arm (e.g., extension arm 40 or extension arm 40*a*) in the extension arm cavity, movably disposing a ratchet block (e.g., ratchet block 70) between a first position and a second position in the ratchet block cavity, allowing movement of the extension arm in an upward direction out of the extension arm cavity and blocking movement of the extension arm in a downward direction into the extension arm cavity by disposing the ratchet block in the first position, and allowing movement of the extension arm both in the upward direction out of the extension arm cavity and the downward direction into the extension arm cavity by disposing the ratchet block in the second position. The exemplary disclosed method may also include rotatably receiving a ratchet drive in a ratchet drive aperture of the base and an aperture of the ratchet block. The exemplary disclosed method may further include translating the ratchet block between the first position and the second position in the ratchet block cavity based on rotating the ratchet drive, which may translate the ratchet block based on ratchet drive threads of the rachet drive being threaded with ratchet block threads of the aperture of the ratchet block. The exemplary disclosed method may also include rotatably receiving a secondary gear in a secondary gear aperture of the base that is aligned with the ratchet drive aperture, and rotating the ratchet drive independently of the secondary gear. Blocking movement of the extension arm in the downward direction into the extension arm cavity by disposing the ratchet block in the first position may include abutting a downward-facing flat surface of a tooth of a ratchet rack of the extension arm against an upward-facing flat surface of a flexible ratchet arm of the ratchet block.

In at least some exemplary embodiments, the exemplary disclosed implant may include a base (e.g., base 20 or base 20*a*) including an extension arm cavity and a ratchet block cavity that intersects the extension arm cavity, an extension arm (e.g., extension arm 40 or extension arm 40*a*) that is movably disposed in the extension arm cavity, and a ratchet block (e.g., ratchet block 70) that is movably disposed between a first position and a second position in the ratchet block cavity. The ratchet block when disposed in the first position may allow movement of the extension arm in an upward direction out of the extension arm cavity and blocks movement of the extension arm in a downward direction into the extension arm cavity. The ratchet block when disposed in the second position may allow movement of the extension arm both in the upward direction out of the extension arm cavity and the downward direction into the extension arm cavity. The ratchet block may include a flexible ratchet arm. The extension arm may include a ratchet rack. The flexible ratchet arm may be aligned with the ratchet rack when the ratchet block is disposed in the first position. The flexible ratchet arm may include a flat surface facing upward away from the extension arm cavity and an angled surface facing downward into the extension arm cavity. The ratchet rack may include a plurality of teeth, each of the plurality of teeth including a flat surface facing downward into the extension arm cavity and an angled surface facing upward away from the extension arm cavity. The exemplary disclosed implant may also include a first plurality of spikes disposed at an upward-facing surface of the extension arm facing away from the extension arm cavity and a second plurality of spikes disposed at a downward-facing surface of a bottom of the base.

The exemplary disclosed system, apparatus, and method may provide an efficient and effective technique for providing for a surgical procedure such as a corpectomy or vertebrectomy procedure. The exemplary disclosed system, apparatus, and method may provide for removing a mechanism of a corpectomy device that prevents collapse when, for example, the corpectomy device is over-expanded or is to be collapsed for removal or replacement.

While multiple embodiments are disclosed, still other embodiments of the present disclosure will become apparent to those skilled in the art from this detailed description. There may be aspects of this disclosure that may be practiced without the implementation of some features as they are described. It should be understood that some details have not been described in detail in order to not unnecessarily obscure the focus of the disclosure. The disclosure is capable of myriad modifications in various obvious aspects, all without departing from the spirit and scope of the present disclosure. Accordingly, the drawings and descriptions are to be regarded as illustrative rather than restrictive in nature.

What is claimed is:

1. An implant, comprising:

a ratchet block disposed in a cavity formed in a sidewall of a base, wherein the ratchet block is positioned within the sidewall to selectively engage with an extension arm that is slidably disposed in the base; and a ratchet drive that is adjustable to move the ratchet block between a first position and a second position within the cavity, wherein the ratchet drive holds the ratchet block in the cavity by extending through the ratchet block and between apertures formed in the cavity.

2. The implant of claim 1, wherein the extension arm is blocked from sliding toward a retracted position within the base when the ratchet block is in the first position.

3. The implant of claim 1, wherein the extension arm is freely slidable between a retracted position within the base and an extended position out of the base when the ratchet block is in the second position.

4. The implant of claim 1, wherein the extension arm includes a ratchet rack and the ratchet block includes a flexible ratchet arm.

5. The implant of claim 4, wherein the flexible ratchet arm is aligned with the ratchet rack when the ratchet block is disposed in the first position.

6. The implant of claim 1, wherein the ratchet block is configured to translate anteriorly-posteriorly within the cavity.

7. The implant of claim 1, wherein the ratchet drive is received in a ratchet block aperture of the ratchet block and the ratchet drive includes ratchet drive threads that are threadable with ratchet block threads of the ratchet block aperture of the ratchet block.

8. The implant of claim 7, further comprising a secondary gear that is rotatably received in a secondary gear aperture of the base, wherein the secondary gear includes a second ratchet drive aperture configured to receive a rear nub of the ratchet drive.

9. The implant of claim 8, wherein the ratchet drive rotates independently of the secondary gear.

10. An implant, comprising:

a base;

a ratchet block disposed in a sidewall of the base;

a ratchet drive having a first end formed with a drive feature and a second end formed with a rear nub, wherein the ratchet drive extends through the ratchet block to retain the ratchet block in the sidewall of the base; and a secondary gear disposed in the base, wherein the secondary gear has a first end formed with a void defining a ratchet drive aperture that receives the rear nub of the ratchet drive.

11. The implant of claim 10, further comprising an extension arm, wherein the extension arm has a ratchet rack that includes a plurality of teeth and the ratchet block further comprises a flexible ratchet arm that selectively engages with a first ratchet rack of the one or more ratchet racks.

12. The implant of claim 11, wherein the secondary gear includes a plurality of secondary gear teeth that mesh with a second rack on the extension arm.

13. The implant of claim 10, wherein the ratchet drive and secondary gear share a common axis of rotation.

14. The implant of claim 10, further comprising:

a ratchet drive retaining pin hole formed in the base; and a ratchet drive retaining pin, wherein the ratchet drive retaining pin is received in the ratchet drive retaining pin hole.

15. The implant of claim 14, further comprising a retaining pin grove formed on the ratchet drive between the drive feature and the rear nub, wherein the ratchet drive retaining pin is configured to seat into the retaining pin groove.

16. An implant, comprising:

a base;

an extension arm slidably disposed in the base, wherein the extension arm includes a plurality of gear racks; and a main gear formed with a first plurality of main gear teeth that mesh with a first gear rack of the plurality of gear racks and a second plurality of main gear teeth that mesh with a second gear rack of the plurality of gear racks, wherein the main gear is rotatably retained within a wall of the base.

17. The implant of claim 16, further comprising:

one or more main gear retaining pin holes formed in the base; and one or more main gear retaining pins, wherein each of the one or more main gear pins is received in one of the one or more main gear retaining pin holes.

18. The implant of claim 17, further comprising a retaining pin recess formed on the main gear between the first plurality of teeth and the second plurality of teeth, wherein the one or more main gear retaining pins are configured to seat into the retaining pin recess.

19. The implant of claim 16, further comprising:

a ratchet block aperture formed in the ratchet block;

a drive feature at a first end of the ratchet drive, ratchet drive threads on a middle portion of the ratchet drive, and a rear nub at a second end of the ratchet drive, wherein the ratchet drive threads are in mechanical communication with ratchet block threads on the ratchet block; and a secondary gear having a first end formed with a void defining a ratchet drive aperture and a middle portion defining a plurality of secondary gear teeth that mesh with a third of the plurality of gear racks, wherein the ratchet drive aperture receives a rear nub of the ratchet drive and the third gear rack is formed on a second face of the extension arm.

20. The implant of claim 19, wherein the rear nub of the ratchet drive rotates within the ratchet drive aperture of the secondary gear to enable the ratchet drive to rotate independently of the secondary gear.

* * * * *